United States Patent [19]

Geisberger et al.

[11] Patent Number: 5,670,687

[45] Date of Patent: Sep. 23, 1997

[54] PROCESS FOR PREPARING SIH-CONTAINING ORGANOCHLOROSILANES

[75] Inventors: Gilbert Geisberger, Altoetting; Tassilo Lindner, Mehring-Oed, both of Germany

[73] Assignee: Wacker-Chemie GmbH, Munich, Germany

[21] Appl. No.: 729,211

[22] Filed: Oct. 15, 1996

[30] Foreign Application Priority Data

Nov. 30, 1995 [DE] Germany .................. 195 44 730.1

[51] Int. Cl.$^6$ .................. C07F 7/08; C07F 7/12
[52] U.S. Cl. .................. 556/469; 502/158; 423/304; 423/325; 423/326; 423/328.2
[58] Field of Search .............. 556/469; 502/158; 423/304, 325, 326, 328.2

[56] References Cited

U.S. PATENT DOCUMENTS

| | | |
|---|---|---|
| 3,399,222 | 8/1968 | Weyenberg . |
| 3,769,310 | 10/1973 | Viego et al. ............... 556/469 |
| 4,567,286 | 1/1986 | Lepage et al. ............. 556/469 |
| 4,613,491 | 9/1986 | Jung et al. . |
| 4,746,752 | 5/1988 | Lepage et al. . |
| 4,775,651 | 10/1988 | Tachikawa et al. . |
| 4,870,200 | 9/1989 | Ottlinger et al. . |
| 4,889,838 | 12/1989 | Lewis et al. ............ 556/469 X |
| 5,209,775 | 5/1993 | Bank et al. . |
| 5,247,110 | 9/1993 | Bank et al. . |
| 5,434,286 | 7/1995 | Geisberger ............... 556/469 |

FOREIGN PATENT DOCUMENTS

| | | |
|---|---|---|
| 0216640 | 4/1987 | European Pat. Off. . |
| 0138670 | 4/1985 | France . |

OTHER PUBLICATIONS

E.L. Zicky, J. Organometal. Chem. 4, pp. 411–412 (1965).
U. Noll, Chemistry and Technology of Silicones, Academic Press, Orlando 1968.
Donald R. Weyenburg et al., in J. Organometal. Chem., (1965), pp. 487–489.
Houben–Weyl, Georg Thieme Verlag, vol. XII/1, pp. 79–80, /1963.
K.G. Alluis, et al., Organometal Chem. 87, Chem 87, 203 (1975).
Derwent Abstract AN 86255303, Mar. 1992.
Derwent Abstract AN 85–100793/17 corresponds to EP-A-0138670 Apr. 1985.

Primary Examiner—Paul F. Shaver
Attorney, Agent, or Firm—Martin Connaughton

[57] ABSTRACT

The invention relates to a process for preparing organosilanes which contain at least one Si-bonded hydrogen in the presence of a phosphonium catalyst, the phosphonium catalyst itself and also a process for its preparation.

9 Claims, No Drawings

PROCESS FOR PREPARING SiH-CONTAINING ORGANOCHLOROSILANES

FIELD OF THE INVENTION

The invention relates to a process for preparing organosilanes which contain at least one Si-bonded hydrogen in the presence of a phosphonium catalyst, the phosphonium catalyst itself and also a process for its preparation.

BACKGROUND OF THE INVENTION

U.S. Pat. Nos. 4,746,752, 3,399,222, 4,775,651 and Donald R. Weyenberg et al., in J. Organometal. Chem., 3 (1965), 487–489 describe processes for preparing organosilanes which are also carried out in the presence of a phosphonium catalyst. In the comproportionation reactions described in the above references, the hydrogen is always transferred to the compound whose silicon atom bears the lower number of organic substituents.

SUMMARY OF THE INVENTION

It is an object of the present invention to provide an improved process for preparing SiH-containing organosilanes, in particular a process in which the end product is obtained in high yields and the hydrogen is transferred in a comproportionation reaction to the compound whose silicon atom bears the larger or equal number of organic substituents.

This object is achieved by means of the present invention.

The invention provides a process for preparing organosilanes which contain at least one Si-bonded hydrogen, which comprises carrying out a comproportionation reaction according to the equation $$ZR_aSiCl_{4-a} + CH_3SiH_cX_{3-c} \rightarrow ZR_aSiH_bCl_{4-a-b} + CH_3SiH_{c-y}X_{3+y-c}$$

where

R is identical or different and is an alkyl, aryl, alkaryl or haloalkyl radical, X is a halogen atom, preferably a chloride ion, bromide ion or iodide ion, a and Z=1 or 2, b=the number of $H_c$ atoms exchanged for chlorine atoms, c=2 or 3, y=the number of chlorine atoms exchanged for $H_c$ atoms in the presence of a catalyst of the formula $$D^+ - E_nX^-, \quad (I)$$

where $D^+$ is a group of the formula $R^1{}_mP^+R^2{}_{4-m}$, where $R^1$ is identical or different and is a monovalent hydrocarbon radical having from 1 to 20 carbon atoms, preferably from 4 to 8 carbon atoms per radical or two radicals R together form a divalent hydrocarbon radical having from 4 to 11 carbon atoms, more preferably from 4 to 6 carbon atoms, which may be interrupted by a heteroatom, $R^2$ is a monovalent or divalent hydrocarbon radical having from 1 to 20 carbon atoms and X is a halogen atom and m=1, 2 or 3, n=0 or 1, where m=3, when n=1, and E is a group of the formula $-Si(OT)_pR^3{}_{3-p}$, where T is a support bound to oxygen, $R^3$ is identical or different and is a monovalent hydrocarbon radical having from 1 to 12 carbon atoms, p is 1, 2 or 3.

The present invention concerns the following comproportionation reactions:

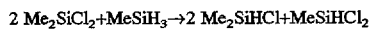

where a=1 or 2.

Preference is given to the reaction:

$$2\ Me_2SiCl_2 + MeSiH_3 \rightarrow 2\ Me_2SiHCl + MeSiHCl_2$$

when a=2, and R is identical or different.

Examples of R are alkyl radicals such as methyl, ethyl, n-propyl, iso-propyl, n-butyl, iso-butyl, tert-butyl, n-pentyl, iso-pentyl, neo-pentyl, tert-pentyl radicals; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical, decyl radicals such as the n-decyl radical; dodecyl radicals such as the n-dodecyl radical; tetradecyl radicals; hexadecyl radicals and octadecyl radicals such as the n-octadecyl radical; cycloalkyl radicals such as cyclopentyl, cyclohexyl and cycloheptyl radicals and methylcyclohexyl radicals; aryl radicals such as the phenyl radical; alkaryl radicals such as o-, m- and p-tolyl radicals; xylyl radicals and ethylphenyl radicals and aralkyl radicals such as the benzyl radical, the α- and β-phenyl radical; haloalkyl radicals such as the chloromethyl, 3-chloropropyl and 3-bromopropyl radicals; haloaryl radicals such as the o-, m-, p-chlorophenyl and chlorotolyl radicals.

Examples of radicals $R^1$ are alkyl radicals such as the methyl, ethyl, n-propyl, iso-propyl, n-butyl, iso-butyl, tert-butyl, n-pentyl, iso-pentyl, neo-pentyl or tert-pentyl radical; hexyl radicals such as the n-hexyl radical; heptyl radicals such as the n-heptyl radical; octyl radicals such as the n-octyl radical and iso-octyl radicals such as the 2,2,4-trimethylpentyl radical; nonyl radicals such as the n-nonyl radical; decyl radicals such as the n-decyl radical; dodecyl radicals such as the n-dodecyl radical; tetradecyl radicals; hexadecyl radicals and octadecyl radicals such as the n-octadecyl radical; cycloalkyl radicals such as cyclopentyl, cyclohexyl and cycloheptyl radicals and methylcyclohexyl radicals; aryl radicals such as the phenyl radical; alkaryl radicals such as o-, m- and p-tolyl radicals; xylyl radicals and ethylphenyl radicals and aralkyl radicals such as the benzyl radical and the α and β-phenylethyl radical. Examples of radicals in which the two radicals $R^1$ together form a divalent hydrocarbon radical are those of the formula —$(CH_2)_5$— and —$(CH_2)_4$—.

Preferred examples of $R^1$ are alkyl radicals, with, owing to the higher catalytic activity, preference given to the n-butyl, n-pentyl, n-hexyl, n-heptyl and n-octyl radicals.

X is a chloride, bromide or iodide ion.

Examples of $R^2$ are divalent hydrocarbon radicals, for example alkylene radicals such as the methylene, ethylene, n-propylene, iso-propylene, n-butylene, iso-butylene, n-pentylene, iso-pentylene radicals; hexylene radicals such as the n-hexylene radical; heptylene radicals such as the n-heptylene radical; octylene radicals such as the n-octylene radical and isooctylene radicals; nonylene radicals such as the n-nonylene radical; decylene radicals such as the n-decylene radical; dodecylene radicals such as the n-dodecylene radical; tetradecylene radicals; hexadecylene radicals and octadecylene radicals such as the n-octadecylene radical; cycloalkylene radicals such as cyclopentylene, cyclohexylene and cycloheptylene radicals; arylene radicals such as the phenylene radical; alkarylene radicals such as tolylene radicals and aralkylene radicals such as the benzylene radical or the corresponding monovalent radicals which have been defined above as divalent radicals for $R^2$.

Preferred examples of $R^2$ as divalent radicals are alkylene radicals, with the n-propylene, n-butylene and n-pentylene radicals being preferred.

Preferred examples of $R^2$ as monovalent radicals are alkyl radicals, with the n-butyl and n-octyl radicals being more preferred.

Examples of $R^3$ are alkyl radicals such as the methyl, ethyl, n-propyl, iso-propyl, n-butyl and iso-butyl radicals; aryl radicals such as the phenyl radical; and alkaryl radicals such as the o-, m- and p-tolyl radicals. Owing to their ready availability, the methyl, ethyl and propyl radicals are preferred as radical $R^3$.

In the catalyst of the formula

 (I), when $D^+$ is a group of the formula $R^1_m P^+ R^2_{4-m}$, where $R^1$ is as defined above, $R^2$ is a monovalent radical as defined above and X is a halogen atom, n=0 and m=1, 2 or 3, the catalyst is a homogeneous catalyst.

Such a homogeneous catalyst is soluble in the reaction medium. These phosphonium salts are used as pure substances, dissolved in a high-boiling inert organic solvent such as tetralin or decalin or dissolved in the starting silane $R_a SiCl_{4-a}$.

Preference is given to (n-butyl)$_3$(n-octyl)PCl.

The homogeneous catalysts have the advantage that they are pumpable as pure substances or in dissolved form. This makes the reaction procedure simpler, since the catalyst can also be metered in while the process is underway, optionally the catalyst concentration can be increased or decreased, the catalyst can be renewed or even replaced by another homogeneous catalyst.

The preparation of such homogeneous catalysts by alkylation of tertiary phosphines with alkyl halides is known from Houben-Weyl, Georg Thieme Verlag, Volme XII/1, p. 79–90, 1963.

The invention further provides the catalyst used in the process of the invention and having formula (I) with n=1.

If in the case of the catalyst of formula

 (I), n=1 and $D^+$ and X are as defined above, then the catalyst is a heterogeneous catalyst which is fixed to a support insoluble in the reaction medium.

Preferred supports insoluble in the reaction medium are selected from the group consisting of zeolites, clays, porous glass, porous ceramic, silicates, porous silicon dioxide such as precipitated and pyrogenic silica, porous aluminum oxide and aluminum silicates.

The support used is preferably open-pored sintered glass (SIRAN®, Schott Glaswerke, Mainz). This open-pored sintered glass has a surface area of up to 0.4 m$^2$/g, preferably 0.4 m$^2$/g, an adjustable pore volume of up to 70%, a pore diameter of from 1.6 μm to 400 μm and contains silanol groups to which silanes can be bound in a hydrolysis-stable manner. This shaped body can be used in the form of round plates, tubes, spheres, rods, honeycombs and preferably Raschig rings.

Other preferred supports, are made of shaped bodies comprising porous silica gel (e.g. KC-Siliperl AF-125 from Kali-Chemie, Hanover). These supports have a specific surface area of 100–700 m$^2$/g, preferably 200–400 m$^2$/g, a pore diameter of from 2 to 15 nm, preferably 10–15 nm, and contain silanol groups to which silanes can be bound in a hydrolysis-stable manner.

The size of the shaped body is preferably from 0.05 to 0.2 times the size of the reaction vessel.

The advantage of the heterogeneous catalyst is that, in contrast to the homogeneous catalyst, no distillation step is necessary to separate off the reaction products, since the heterogeneous catalyst remains in the reactor. This is important in the case of relatively high-boiling silanes such as phenylsilanes, since in the homogeneously catalyzed procedure it is not possible to carry out the reaction and distillation in one reaction vessel.

The heterogeneous catalyst is prepared by reacting a compound of formula

 (II), where $R^1$, $R^2$, $R^3$, X are as defined above, m=3, p=1, 2 or 3 and Y is a hydrolyzable group which is identical or different, in an inert solvent such as toluene, chlorobenzene or an alcohol, preferably isopropanol, at temperatures in the range of from 0° to 200° C., preferably in the range from 50° to 100° C., with a support.

Examples of such hydrolyzable groups Y are alkoxy radicals such as the methoxy, ethoxy, propoxy and butoxy radicals, with the ethoxy radical being preferred, and halogen atoms such as the chlorine atom.

An example of a preferred compound of formula II is triethoxysilyl-3-propyl-N,N,N-tributylphosphonium chloride. Preference is given to using 5%–40% by weight, in particular 25%–30% by weight, of compounds of formula (II), based on the weight of the untreated support which can be employed as powder or preferably as finished shaped bodies in the form of round plates, tubes, spheres, rods, honeycombs and preferably Raschig rings.

Preference is given to using a 10%–60% strength, preferably a 25%–35% strength, solution of the compound of formula (II) in alcohol such as methanol, preferably isopropanol or other inert solvents such as toluene, xylene and chlorobenzene based on the weight of the untreated support.

The compound of formula (II) is bound to the support in the presence or absence of water (formation of hydrolysates of the compound of formula (II); are known, cf. K. G. Allumet et al., Organometal. Chem 87, Chem. 87, 203 (1975)) and are carried out in the presence or absence of additives such as water glass, titanium halides or titanium alkoxides, zirconium halides or zirconium alkoxides, aluminum halides or aluminum alkoxides, silicon halides or silicon alkoxides and tin halides or tin alkoxides, with preference to tetraalkoxysilanes such as tetramethoxysilane, tetraethoxysilane, tetrapropoxysilane and tetrabutoxysilane and more preferably tetraethoxysilane.

Another way is to first partially hydrolyze the compound of formula (II) and only in a second step in the presence of the support to completely hydrolyze it and thus bind it to the support.

To modify the hydrolysates, the hydrolysis can also be carried out in the presence of additives such as water glass, titanium halides or titanium alkoxides, zirconium halides or zirconium alkoxides, aluminum halides or aluminum alkoxides, silicon halides or silicon alkoxides and tin halides or tin alkoxides, with preference given to tetraalkoxysilanes such as tetramethoxysilane, tetraethoxysilane, tetrapropoxysilane and tetrabutoxysilane and more preferably to tetraethoxysilane.

The compounds for modifying the hydrolysates are used in molar ratios to the compounds of formula (II) of from 1:1 to 5:1, preferably 3:1.

Examples of the compounds used in the preparation of the hydrolysates are $Si(OEt)_4$ and $(EtO)_3SiCH_2CH_2CH_2PBu_3^+Cl^-$;
$Ti(OBu)_4$ and $(MeO)_3SiCH_2CH_2CH_2PMe_2C_{18}H_{37}^+Cl^-$;
$Na_2SiO_3$ and $(MeO)_3SiCH_2CH_2CH_2PMe_2C_{10}H_{21}^+Cl^-$;
$Al(O-i-Pr)_3$ and $(MeO)_3SiCH_2CH_2CH_2PMe_3^+Cl^-$, where
Me is a methyl radical,
Et is an ethyl radical,
i-Pr is an isopropyl radical and
Bu is an n-butyl radical.

The catalyst obtained is dried at a temperature of from 50° to 100° C.

The catalysts can be in the form of powder having a mean particle size of from 1 µm to 1 mm, preferably from 0.5 to 1 mm, and comprising compounds of formula (II) bound to the support or may have been converted in a manner known, before or after binding the compounds of formula (II) to the support, into shaped bodies such as rings, half rings, rods, spheres, cubes or saddles. Preferred shaped bodies are in the form of rings, spheres or cubes.

The bodies are shaped from finely divided catalyst having a mean particle size of from 1 µm to 1 mm, with or without addition of organic or inorganic binders or crosslinking hydrolysis. Shaping can be carried out by means of pressing at elevated temperature or by means of sintering at elevated pressure, but also by means of an extruder and subsequent comminution of the profiles.

Examples of organic or inorganic binders are epoxy resins, water glass, organic polymers such as polyethylene, polypropylene, polystyrene, polyvinyl chloride, polyacrylate and polyamide.

To increase the porosity of the shaped catalysts, a water-soluble substance such as sodium chloride or sodium sulfate is added to the compositions prior to shaping, and this substance is then dissolved out after the shaping step to give a highly active macroporosity.

Preference is given to using as support open-pored sintered glass (SIRAN®, Schott Glaswerke, Mainz). This open-pored sintered glass has a surface area of up to 0.4 m²/g, preferably 0.4 m²/g, an adjustable pore volume of up to 70%, a pore diameter of from 1.6 µm to 400 µm and contains silanol groups to which silanes can be bound in a hydrolysis-stable manner. This shaped body can be used in the form of round plates, tubes, spheres, rods, honeycombs and preferably Raschig rings. The size of the shaped body is from 0.05 to 0.2 times the size of the reaction vessel.

The compounds of formula (II) are bound to the support surface by impregnating the shaped bodies with compounds of formula (II), preferably in admixture with additives such as silicon alkoxides, in alcohols such as ethanol with crosslinking hydrolysis. Use is made of 5%–40% by weight, in particular 25%–35% by weight, of compounds of formula (II), based on the weight of the untreated support which can be employed as powder or as finished shaped bodies in the form of round plates, tubes, spheres, rods, honeycombs and preferably Raschig rings. Preference is given to using a 10%–60% strength, more preferably a 25%–35% strength, solution of the compound of formula (II) in alcohols such as methanol, preferably ethanol, or other inert solvents such as toluene.

The compound of formula (II) is used together with a compound for modifying the hydrolysates, for example silicon alkoxides in molar ratios of from 1:1 to 1:5, preferably 1:3. The subsequent crosslinking hydrolysis is achieved by addition of dilute hydrochloric acid and by increasing the reaction temperature to at most 100° C., with the solvent distilling off and the catalyst remaining as residue. For complete drying, the catalyst is flushed with air at up to 90° C.

The catalyst of the invention is in the form of a shaped body and preferably has a size which is from 0.05 to 0.2 times the diameter of the reaction vessel.

In the process of the invention, the phosphonium catalysts have excellent thermal stability in the various organochlorosilane media and high catalytic activity in the comproportionation reactions of the invention.

The methylsilane and/or methylchlorosilane used in the process of the invention is prepared by disproportionation of methyldichlorosilane in the presence of a catalyst as described in U.S. Pat. No. 4,870,200.

The methylsilane and methylchlorosilane used in the process of the invention can also be prepared by other methods.

As second preferred support, use is made of shaped bodies of porous silica gel (e.g. KC-Siliperl AF-125 from Kali-Chemie, Hanover). These supports have a specific surface area of 100–700 m²/g, preferably 200–400 m²/g, a pore diameter of from 2 to 15 nm, preferably 10–15 nm, and contain silanol groups to which silanes can be bound in a hydrolysis-stable manner.

The compounds of formula (II) are bound to the support surface by impregnating the shaped bodies with compounds of formula (II) in alcohol such as isopropanol with crosslinking hydrolysis. Preference is given to using 10%–60% by weight, in particular 30%–50% by weight, of compounds of formula (II), based on the weight of the untreated support which can be employed as powder or as finished shaped bodies, preferably in the form of spheres. Preference is given to using a 5%–60% strength, preferably a 10%–30% strength, solution of the compound of formula (II) in alcohol, preferably isopropanol, or other inert solvents such as toluene. The crosslinking hydrolysis is achieved by addition of aqueous ammonia and by increasing the reaction temperature to at most 100° C. Subsequently, the supernatant solution is decanted off and the catalyst remaining as residue is washed and dried.

The methylsilane used in the process of the invention can be prepared, for example, from methylhydrogensiloxanes by the method described in E. L. Zicky, J. Organometal. Chem. 4, 411–412 (1965) or by hydrogenation of methylchlorosilanes with metal hydrides as described in W. Noll, Chemie und Technologie der Silicone, Verlag Chemie, Weinheim, 2nd Edition, pages 76 to 77, 1968.

The silane starting materials are used in gaseous or liquid form or dissolved in an inert organic solvent such as hexane, toluene, xylene or chlorobenzene.

In a preferred homogeneous procedure, the vertical, thermostatic reaction tube is charged with the catalyst of formula $$D^+ \text{—} E_n X \text{—}, \qquad (I),$$

where $D^+$ is a group of the formula $R^1_m P^+ R^2_{4-m}$,
where
$R^1$ and $R^2$ are as defined above and
X is a halogen atom,
n=0 and
m=1, 2 or 3, with or without solvent, and methylsilane and/or methylchlorosilane together with the silane $R_a SiCl_{4-a}$ are passed in at a pressure of from 0.1 to 20 bar, preferably from 1 to 3 bar, and a temperature of from 0° to 250° C., preferably from 50° to 120° C. The molar ratio of starting materials for methylsilane/$R_a SiCl_{4-a}$ is from 0.1 to 10, preferably from 0.3 to 1.0. The molar ratio of starting materials for methylchlorosilane/$RaSiCl_{4-a}$ is from 0.1 to 15, preferably from 0.5 to 1.5. The catalyst concentration in the silane is from 0.1% to 80% by weight, preferably from 2% to 60% by weight, more preferably from 30% to 60% by weight. In the preparation of SiH-containing organochlorosilanes having low boiling points (e.g. $Me_2SiHCl$ or $EtSiHCl_2$), the silanes distill from the reaction tube (fill level remains constant), the reaction mixture is condensed and subsequently fractionated by distillation. In the case of organochlorosilanes having relatively high boiling points, the reaction mixture is taken off at an overflow in the upper part of the reactor. This also results in discharge of the catalyst. To keep the catalyst concentration in the reactor constant, the appropriate amount is dissolved in the starting silane $R_a SiCl_{4-a}$ and metered in.

In a second process variant, the heterogeneous catalyst is used in finely divided form in a fixed or fluidized bed or preferably as shaped bodies present in a thermostatic tube. When the catalyst is in the form of shaped bodies, methylsilane and/or methylchlorosilane together with the silane $R_a SiCl_{4-a}$ are passed in at a pressure of from 0.1 to 20 bar, preferably from 1 to 3 bar, and a temperature of from 0° to 250° C., preferably from 100° to 120° C. The molar ratio of starting materials for methylsilane/$R_a SiCl_{4-a}$ is from 0.1 to 10, preferably from 0.3 to 1.0. The molar ratio of starting materials for methylchlorosilane/$R_a SiCl_{4-a}$ is from 0.1 to 15, preferably from 0.5 to 1.5. The reaction mixture obtained is subsequently fractionated by distillation. Selection of a suitable starting material ratio methylsilane/organochlorosilane enables the monohydrogenated silane $R_a SiHCl_{3-a}$ (e.g. $Me_2SiHCl$ or $PhSiHCl_2$) desired as target product to be obtained in high yields. Increasing the starting material ratio also makes possible the preparation of dihydrogen silanes (e.g. $PhSiH_2Cl$).

The process of the invention can be carried out batchwise, semicontinuously or fully continuously. It is preferably carried out fully continuously. The SiH-containing organochlorosilanes are valuable starting compounds for preparing functional silanes or siloxanes which are obtained via a hydrosilylation reaction with organic compounds having aliphatic double or triple bonds. A further use of dimethylchlorosilane is the preparation of organopolysiloxanes containing dimethyl hydrogensilyl groups, which are used in addition-cross-linking silicone rubber compositions.

The methyltrichlorosilane obtained as by-product, mainly in the disproportionation of methyldichlorosilane, can also be utilized in an economical manner, for example for preparing finely divided silica produced by flame hydrolysis.

In the following formulae,
Me denotes methyl,
Bu denotes butyl,
Ph denotes phenyl and
P denotes phosphorus.

EXAMPLE 1

Preparation of the heterogeneous catalyst:

100 g of porous silicon dioxide in spherical form having a diameter of 3–5 mm, KC-Siliperl AF 125 (Kali-Chemie, Hannover, Germany), were admixed with a solution of 50 g of triethoxysilylpropyltributylphosphonium chloride (prepared by the equimolar reaction of tributylphosphine with chloropropyltriethoxy-silane at 110° C./2 days) and 10 ml of aqueous ammonia (25% strength) in 400 ml of iso-propanol and kept at 80° C. for 24 hours. The solid was then filtered off from the solvent and the now functionalized support was dried (weight increase as a result of coating 14.4%).

EXAMPLE 2

The catalyst prepared as described in Example 1 was placed in a vertical thermostatic tube (2.4 cm diameter, 150 cm length) to a height of 120 cm. At a column temperature of 61° C., 100 g/h of liquid dimethyldichlorosilane and 6 liter/h of gaseous methylsilane were fed in continuously at the bottom of the bubble column. The distillate leaving the top of the column was condensed and the composition was determined by $^1$H-NMR spectroscopy.

| $MeSiH_3$ | 8 mol % | $Me_2SiH_2$ | 1 mol % |
|---|---|---|---|
| $MeSiH_2Cl$ | 9 mol % | $Me_2SiHCl$ | 23 mol % |
| $MeSiHCl_2$ | 9 mol % | $Me_2SiCl_2$ | 51 mol % |
| $MeSiCl_3$ | 0 mol % | | |

EXAMPLE 3

A vertical, heatable tube of V4A steel having an internal diameter of 5 cm and a total length of 250 cm was charged with V4A steel Interpak 10 packing. The catalyst used in the subsequent reaction was $Bu_3 octylPCl$ (prepared by equimolar reaction of $Bu_3P$ with octyl chloride at 110° C./48 hours) in the form of a 2% strength solution in $PhSiCl_3$.

At a total pressure of 2.2 bar (abs.) and an internal temperature of 70° C., 1400 g/h of the $PhSiCl_3$/$Bu_3 octylPCl$ solution (liquid) and 69 g/h of gaseous $MeSiH_3$ were metered continuously into the lower end of the reaction column.

The product mixture was taken on in liquid form at a column height of about 200 cm and the composition was determined by $^1$H-NMR spectroscopy.

| $MeSiH_2Cl$ | 0 mol % | $PhSiH_2Cl$ | 3 mol % |
|---|---|---|---|
| $MeSiHCl_2$ | 8 mol % | $PhSiHCl_2$ | 43 mol % |
| $MeSiCl_3$ | 10 mol % | $PhSiCl_3$ | 36 mol % |

This gave 610 g/h of the target product $PhSiHCl_2$, the conversion of the $PhSiCl_3$ used was 52%. The product mixture was worked up by distillation, with $PhSiHCl_2$ being obtained in a purity of 97%.

EXAMPLE 4

The procedure of Example 3 was repeated, but 133 g/h of MeSiH₃ were metered in instead of 69 g/h. The product mixture had the following composition:

| | | | |
|---|---|---|---|
| MeSiH₂Cl | 2 mol % | PhSiH₃ | 1 mol % |
| MeSiHCl₂ | 20 mol % | PhSiH₂Cl | 11 mol % |
| MeSiCl₃ | 8 mol % | PhSiHCl₂ | 48 mol % |
| | | PhSiCl₃ | 11 mol % |

Under these experimental conditions, 815 g/h of PhSiHCl₂ were obtained, the PhSiCl₃ conversion into PhSiHCl₂ was 69%.

EXAMPLE 5

A vertical thermostatic tube (2.4 cm diameter, 150 cm height) was filled completely with the catalyst prepared as described in Example 1. At a column temperature of 70° C., 150 g/h of liquid diphenyldichlorosilane and about 5 l/h of gaseous methylsilane were continuously fed in at the bottom of the bubble column. The liquid/gas mixture leaving the top of the column was cooled to room temperature and the composition of the silane mixture was determined by ¹H-NMR spectroscopy:

| | | | |
|---|---|---|---|
| MeSiH₃ | 7 mol % | Ph₂SiH₂ | 1 mol % |
| MeSiH₂Cl | 12 mol % | Ph₂SiHCl | 33 mol % |
| MeSiHCl₂ | 10 mol % | Ph₂SiCl₂ | 36 mol % |
| MeSiCl₃ | 1 mol % | | |

This gave 61 g/h of the target product Ph₂SiHCl, which was obtained after work-up by distillation in a purity of 95%.

EXAMPLE 6

A vertical, heatable reactor of V4A steel, having an internal diameter of 40 cm and a total length of 500 cm, was filled to a height of 200 cm with V4A Pall rings (1 inch).

As catalyst, 100 kg of Bu₄PCl in the form of a 50% strength solution in Me₂SiCl₂ were pumped into the reactor. At a total pressure of 1.9 bar and an internal temperature of 82° C., 7 kg/h of MeSiH₃ and 85 kg/h of Me₂SiCl₂ were metered continuously into the lower end of the reactor. The fill level of the bubble column was thereby kept constant and the product mixture obtained at the top of the reactor was fed to a continuously operated distillation column. MeSiH₃ and MeSiH₂Cl were taken off in gas form at the top of this column and recirculated to the reactor to be reacted further. At the lower end of the column, 92 kg/h of silane mixture having the following composition were taken off continuously in liquid form:

| | |
|---|---|
| MeSiH₂Cl | 0.2% by weight |
| Me₂SiHCl | 27.3% by weight |
| MeSiHCl₂ | 17.7% by weight |
| MeSiCl₃ | 0.6% by weight |
| Me₂SiCl₂ | 54.2% by weight |

This silane mixture was further worked up by distillation, giving Me₂SiHCl in a purity of 99%. The reactor was able to be operated over a period of 3 months without a decrease in the catalytic activity being found.

What is claimed is:

1. A process for preparing organosilanes which contain at least one Si-bonded hydrogen, which comprises carrying out a reaction according to the equation $$ZR_aSiCl_{4-a} + CH_3SiH_cX_{3-c} \rightarrow ZR_aSiH_bCl_{4-a-b} + CH_3SiH_{c-y}X_{3+y-c}$$

where
R is identical or different and an alkyl, aryl, alkaryl or haloalkyl radical,
X is a halogen atom,
a and Z=1 or 2,
b=the number of $H_c$ atoms exchanged for chlorine atoms,
c=2 or 3, and
y=the number of chlorine atoms exchanged for $H_c$ atoms in the presence of a catalyst of formula $$D^+ \text{---} E_n X^-, \tag{I}$$

where $D^+$ is a group of the formula $R^1_m P^+ R^2_{4-m}$,
where
$R^1$ is identical or different and is a monovalent hydrocarbon radical having from 1 to 20 carbon atoms per radical or two radicals R together form a divalent hydrocarbon radical having from 4 to 11 carbon atoms, which may be interrupted by a heteroatom,
$R^2$ is a monovalent or divalent hydrocarbon radical having from 1 to 20 carbon atoms and
X is a halogen atom and
m=1, 2 or 3,
n=0 or 1, where m=3, when n=1, and
E is a group of the formula $-Si(OT)_p R^3_{3-p}$,
where
T is a support bound to oxygen and
$R^3$ is a monovalent hydrocarbon radical having from 1 to 12 carbon atoms,
p=1, 2 or 3.

2. The process as claimed in claim 1, wherein the support to which the catalyst is bound is selected from the group consisting of zeolites, clays, porous glass, porous ceramic, silicates, porous silicon dioxide such as precipitated and pyrogenic silica, porous aluminum oxide and aluminum silicates.

3. A catalyst having the formula $$D^+ \text{---} E_n X^-, \tag{I}$$

where
$D^+$ is a group of the formula $R^1_m P^+ R^2_{4-m}$,
where
$R^1$ is identical or different and is a monovalent hydrocarbon radical having from 1 to 20 carbon atoms per radical or two radicals R together form a divalent hydrocarbon radical having from 4 to 11 carbon atoms, which may be interrupted by a hetero atom,
$R^2$ is a monovalent or divalent hydrocarbon radical having from 1 to 20 carbon atoms and
X is a halogen atom and
m=1, 2 or 3,
n=0 or 1, where m=3, when n=1, and
E is a group of the formula $-Si(OT)_p R^3_{3-p}$,
where
T is a support bound to oxygen and
$R^3$ are identical or different and are each a monovalent hydrocarbon radical having from 1 to 12 carbon atoms and
p is 1, 2 or 3.

4. A catalyst as claimed in claim 3, wherein the support to which the catalyst is bound is selected from the group consisting of zeolites, clays, porous glass, porous ceramic, silicates, porous silicon dioxide porous aluminum oxide and aluminum silicates.

5. A process for preparing a heterogeneous catalyst as claimed in claim 3, which comprises reacting a compound of formula

  (II)

where
- $R^1$, $R^2$, $R^3$, X are as defined above,
- m=3 and
- p=1, 2 or 3 and
- Y is a hydrolyzable group which is identical or different, in a solvent, with a support.

6. A process for preparing a heterogeneous catalyst as claimed in claim 5, wherein the support to which the catalyst is bound is selected from the group consisting of zeolites, clays, porous glass, porous ceramic, silicates, porous silicon dioxide, porous aluminum oxide and aluminum silicates.

7. A catalyst as claimed in claim 4, wherein the porous silicon dioxide is a precipitated silica or pyrogenic silica.

8. A process for preparing a heterogeneous catalyst as claimed in claim 6, wherein the porous silicon dioxide is a precipitated silica or pyrogenic silica.

9. A process as claimed in claim 5, where in a first step the compound of formula (I) is partially hydrolyzed and in a second step the hydrolysis is completed in the presence of a support.

* * * * *